(12) United States Patent
Foley et al.

(10) Patent No.: US 7,004,162 B1
(45) Date of Patent: Feb. 28, 2006

(54) EXHALATION VALVE

(75) Inventors: Martin P. Foley, London (CA); Robert Morton, London (CA)

(73) Assignee: Canadian Monaghan, Ltd., London (CA)

( * ) Notice: Subject to any disclaimer, the term of this patent is extended or adjusted under 35 U.S.C. 154(b) by 0 days.

(21) Appl. No.: 09/409,792

(22) Filed: Sep. 30, 1999

Related U.S. Application Data

(63) Continuation of application No. 08/842,956, filed on Apr. 25, 1997, now Pat. No. 5,988,160, which is a continuation of application No. 08/270,752, filed on Jul. 5, 1994, now Pat. No. 5,645,049, which is a continuation-in-part of application No. 07/973,280, filed on Nov. 9, 1992, now abandoned.

(51) Int. Cl.
*A61M 11/00* (2006.01)

(52) U.S. Cl. .......................... 128/200.22; 128/200.14; 128/200.23; 128/203.29

(58) Field of Classification Search ........... 128/200.14, 128/200.22, 200.23, 203.12, 204.11, 204.12, 128/203.29
See application file for complete search history.

(56) References Cited

U.S. PATENT DOCUMENTS

| | | | | |
|---|---|---|---|---|
| 217,691 A | * | 7/1879 | Hurd | 128/203.29 |
| 302,949 A | * | 8/1884 | Skene | 128/203.29 |
| 346,367 A | * | 7/1886 | Genese | 128/203.29 |
| 374,831 A | * | 12/1887 | Harrington | 128/207.12 |
| 379,042 A | * | 3/1888 | Battershall | 128/203.29 |
| 440,713 A | | 11/1890 | Krohne et al. | |
| 533,127 A | * | 1/1895 | Horton | 128/203.29 |
| 590,376 A | * | 9/1897 | Pickin | 128/203.25 |
| 731,973 A | | 6/1903 | Teter | |
| 733,027 A | | 7/1903 | Goldan | |
| 756,354 A | * | 4/1904 | Goldan | 128/203.29 |
| 812,706 A | | 2/1906 | Warbasse | |
| 1,007,644 A | | 10/1911 | Cocke | |
| 1,221,387 A | | 4/1917 | Marie | |
| 1,671,010 A | | 5/1928 | Breacklein | |
| 1,695,170 A | | 12/1928 | Burdick | |
| 1,998,327 A | | 4/1935 | McGuire | |
| 2,029,129 A | * | 1/1936 | Schwartz | 128/206.15 |
| 2,070,241 A | * | 2/1937 | Schwartz | 128/206.17 |
| 2,164,330 A | | 7/1939 | Katz et al. | |
| 2,238,964 A | * | 4/1941 | Benos | 128/206.15 |
| 2,344,669 A | | 3/1944 | Barker et al. | |
| 2,381,568 A | | 8/1945 | Booharin | |
| 2,432,946 A | | 12/1947 | Theunissen | |
| 2,445,347 A | * | 7/1948 | Marcel | 128/203.27 |

(Continued)

FOREIGN PATENT DOCUMENTS

AR  244490  11/1993

(Continued)

*Primary Examiner*—Aaron J. Lewis
(74) *Attorney, Agent, or Firm*—Brinks Hofer Gilson & Lione

(57) ABSTRACT

A mask is provided for the inhalation of medication, such as asthmatic medication. The mask is molded of a resilient plastic or rubber material and has a central through opening and includes an open front portion adapted to receive an aerosolization chamber which receives medication from a metered dose inhaler. A sidewall expands outwardly from the open front portion and is adapted to fit sealingly on a face covering the mouth and nose. The sidewall is provided with an extension to accommodate the nose. A one-way exhalation valve is provided in the mask, preferably at the far end of the nose accommodating extension for conveying exhaled air to the outside, and preventing entrance of outside air therethrough into said mask.

20 Claims, 2 Drawing Sheets

U.S. PATENT DOCUMENTS

| | | | |
|---|---|---|---|
| 2,843,119 A | 7/1958 | Glasser | |
| 2,848,994 A | 8/1958 | Aguado | |
| 2,888,012 A | 5/1959 | Larson | |
| 2,893,397 A | 7/1959 | Plehn | |
| 2,931,356 A | 4/1960 | Schwartz | |
| 2,985,169 A | 5/1961 | Elling | |
| 3,027,896 A * | 4/1962 | Newton | 128/204.13 |
| 3,124,124 A | 3/1964 | Cross | |
| 3,182,659 A | 5/1965 | Blount | |
| 3,232,292 A | 2/1966 | Schaefer | |
| 3,490,452 A | 1/1970 | Greenfield | |
| 3,491,755 A | 1/1970 | Barghini et al. | |
| 3,556,122 A | 1/1971 | Laerdal | |
| 3,707,966 A * | 1/1973 | Nebel | 128/204.17 |
| 3,889,671 A * | 6/1975 | Baker | 128/207.13 |
| 4,002,167 A | 1/1977 | Rambosek | |
| 4,016,878 A | 4/1977 | Castel et al. | |
| 4,071,026 A * | 1/1978 | Bevins | 128/205.29 |
| 4,080,664 A * | 3/1978 | Morris et al. | 128/206.15 |
| 4,470,412 A | 9/1984 | Nowacki et al. | |
| 4,546,768 A | 10/1985 | Ferierabend | |
| 4,573,463 A | 3/1986 | Hall | |
| 4,637,387 A | 1/1987 | Hall | |
| 4,705,033 A * | 11/1987 | Halfpenny | 128/201.13 |
| 4,722,334 A | 2/1988 | Balckmer et al. | |
| 4,770,169 A | 9/1988 | Schmoegner et al. | |
| 4,809,692 A | 3/1989 | Nowacki et al. | |
| 4,811,730 A | 3/1989 | Milano | |
| 4,819,628 A | 4/1989 | Eisenberg et al. | |
| 4,832,015 A | 5/1989 | Nowacki et al. | |
| 4,850,346 A | 7/1989 | Michel et al. | |
| 4,858,605 A | 8/1989 | Levy | 128/203.11 |
| 4,865,027 A | 9/1989 | Laanen et al. | |
| 4,886,055 A | 12/1989 | Hoppough | |
| 4,938,209 A | 7/1990 | Fry | |
| 5,012,803 A | 5/1991 | Foley et al. | |
| 5,012,804 A | 5/1991 | Foley et al. | |
| 5,062,423 A | 11/1991 | Matson et al. | |
| 5,109,839 A | 5/1992 | Blasdell et al. | |
| 5,186,165 A | 2/1993 | Swann | |
| 5,231,982 A * | 8/1993 | Harrison et al. | 128/207.12 |
| 5,311,862 A | 5/1994 | Blasdell et al. | |
| 5,497,765 A | 3/1996 | Praud et al. | |
| 5,535,741 A | 7/1996 | Widerstrom et al. | |
| 5,586,551 A | 12/1996 | Hilliard | |
| 5,645,049 A | 7/1997 | Foley et al. | |
| D388,873 S | 1/1998 | Richards et al. | |
| 5,730,722 A | 3/1998 | Wilk | |
| 5,765,553 A | 6/1998 | Richards et al. | |
| 5,881,718 A | 3/1999 | Mortensen et al. | |
| 5,954,049 A | 9/1999 | Foley et al. | |
| 5,988,160 A | 11/1999 | Foley et al. | |
| 6,192,876 B1 | 2/2001 | Denyer et al. | |
| 6,206,003 B1 | 3/2001 | Burch | |
| 2002/0170557 A1 | 11/2002 | Schmidt | |

FOREIGN PATENT DOCUMENTS

| | | | |
|---|---|---|---|
| AU | B-16114/92 * | 11/1992 | 128/203.12 |
| CA | 1220111 | 4/1987 | |
| CA | 2092614 | 3/1992 | |
| DE | 726 282 | 10/1942 | |
| DE | 30 00 518 | 7/1981 | |
| EP | 0 139 363 A1 | 5/1985 | |
| EP | 514085 A1 * | 11/1992 | 128/203.12 |
| EP | 0 601 708 A2 | 11/1993 | |
| FR | 336.052 | 2/1904 | |
| FR | 812.329 | 5/1937 | |
| GB | 531805 | 1/1941 | |
| GB | 2 230 456 A | 10/1990 | |

* cited by examiner

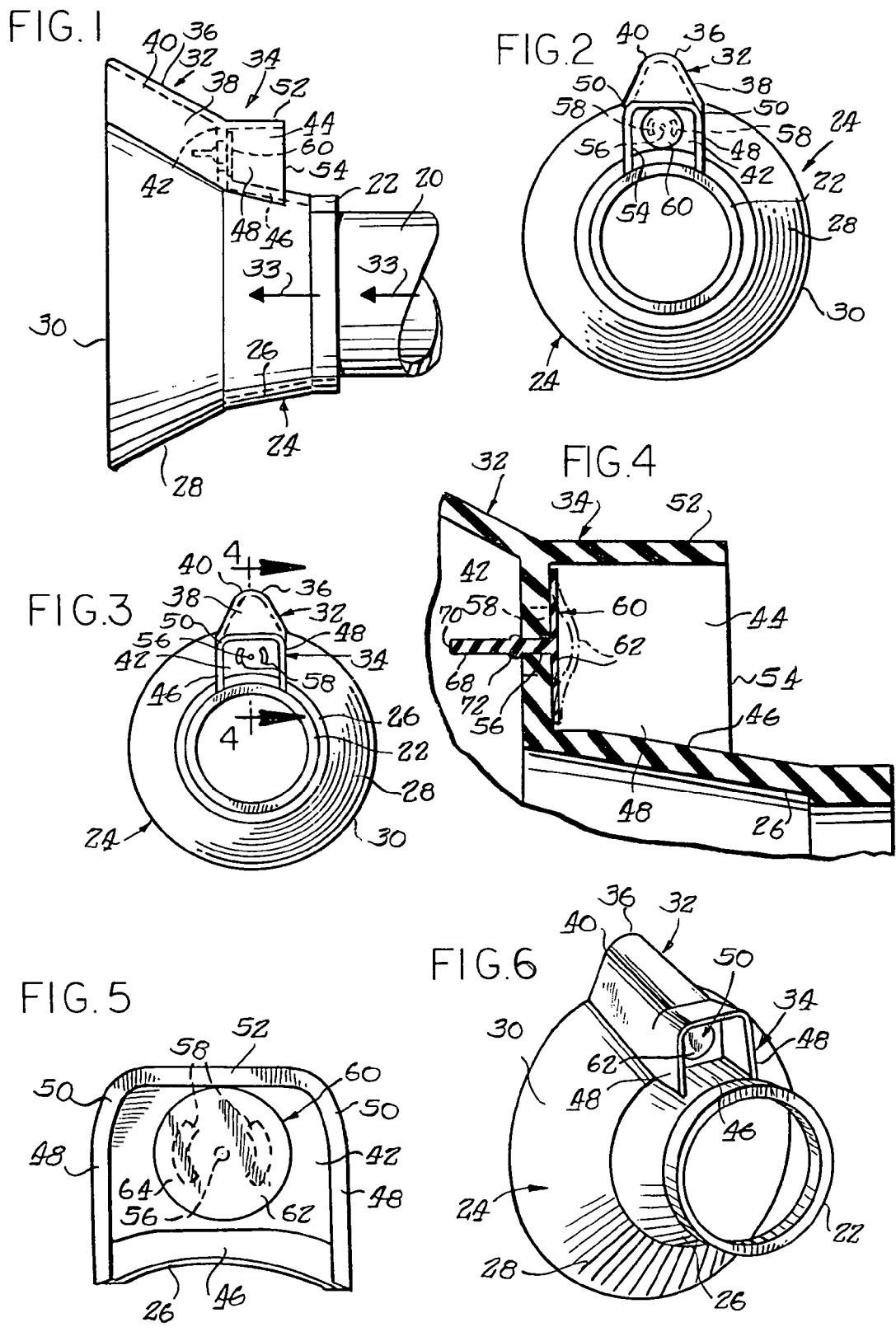

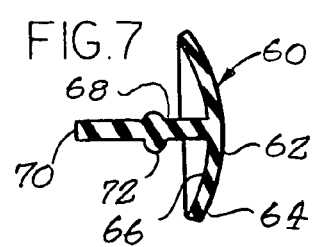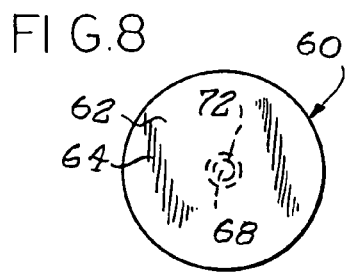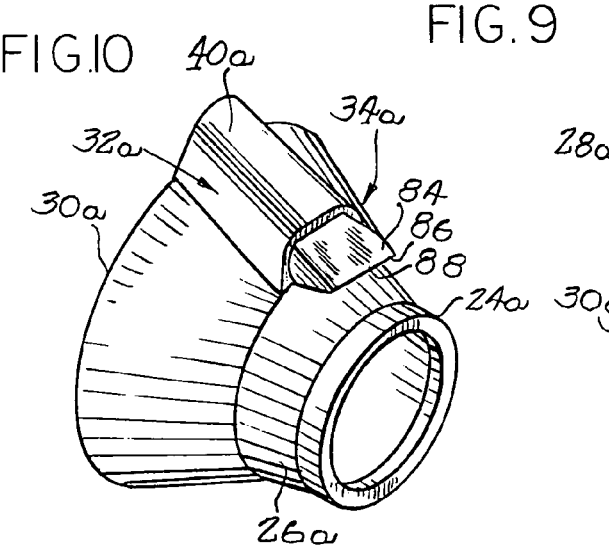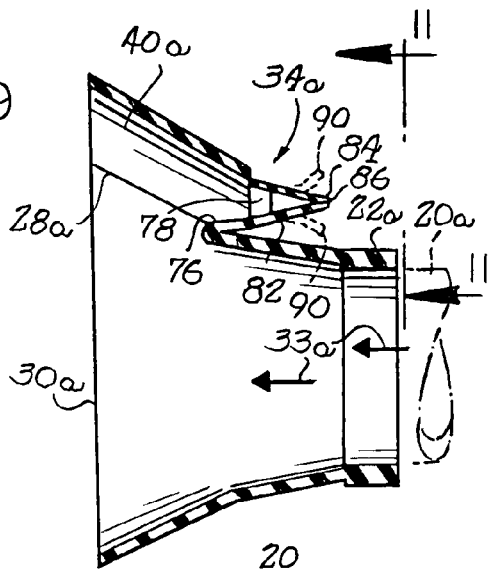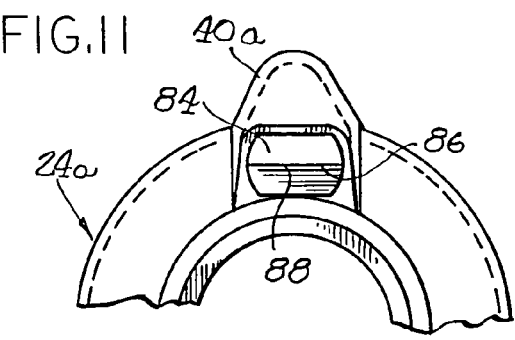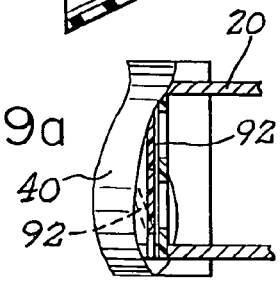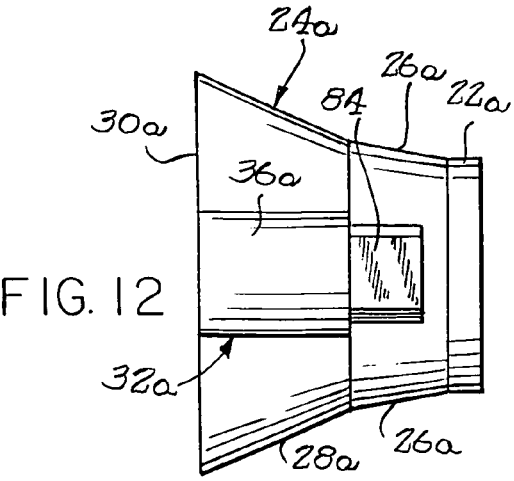

EXHALATION VALVE

This is a continuation of U.S. Ser. No. 08/842,956, filed Apr. 25, 1997, now U.S. Pat. No. 5,988,160, which is a continuation of U.S. Ser. No. 08/270,752, filed on Jul. 5, 1994, now U.S. Pat. No. 5,645,049, which is a continuation-in-part of U.S. Ser. No. 07/973,280, filed Nov. 9, 1992, abandoned, wherein U.S. Ser. No. 08/842,956 and U.S. Ser. No. 08/270,752 are hereby incorporated herein by reference.

BACKGROUND OF THE INVENTION

Breathing problems due to alergies, asthma, etc. are widespread. It is known that such problems can be helped with inhalation of appropriate medication, such as a beta agonist. Small cartridges containing such medication are provided. Each cartridge has a valve which when activated dispenses a predetermined quantity of medication as a spray. Such devices are known as metered dose inhalers (MDI). Such metered dose inhalers are rather inefficient in delivering the medication to the patient. It is known that provision of some sort of an inhalation chamber between the MDI and the patient's mouth materially improves-delivery to the patient. One such device that has met rather considerable commercial success is disclosed and claimed in Nowacki et al U.S. Pat. No. 4,470,412.

Further problems are encountered with delivery of anti-asthmatic medication to children. With adults in otherwise reasonably good health the patient generally can be relied upon to handle the matter himself, or to communicate with a healthcare provider. However, children, particularly infants, cannot readily follow directions, and often cannot communicate with a healthcare provider. Accordingly, efforts have been made so that a healthcare provider can readily observe whether a small child or infant is properly inhaling and exhaling, and thereby taking in the necessary medication. Two inhalers for this purpose are shown in Nowacki et al U.S. Pat. No. 4,809,692 and in Nowacki et al U.S. Pat. No. 4,832,015. It has been found in practice that anxious mothers often produce false readings with infants and other small children, and it further has been found that producing requisite plastic moldings at a commercially acceptable cost has been difficult.

In the last two U.S. patents noted above a small mask is attached to the exit end of the aerosolizing chamber to engage an infant's face to ensure proper movement of the vaporized or aerosolized medication from the chamber into the patient's mouth and nose. Such mask is generally made of a plastic or rubber material. In the first of these two patents a whistle is provided that operates upon inhalation or exhalation of the patient (or both) so that a sound will be produced that can be observed by a healthcare provider. However, the sound is not very loud, and is sometimes indiscernable in conditions of relatively high ambient noise levels. In the second of such two patents a bubble of thinner material is formed integral with the mask, and is intended to move in and out with inhalation and exhalation. The bubble must be thin enough to flex readily, but not so thin as to tear or otherwise fracture. Molding of the mask to produce a relatively thick mask, and the extremely thin integral bubble is difficult.

It will be recognized that a person who is elderly, or who is sick, or who is in some manner incapacitated may present many of the same problems of communicating with or being observed by a healthcare provider as with infants.

OBJECTS OF THE PRESENT INVENTION

In accordance with the principles of the present invention it is an object thereof to provide a mask for inhalation of medication, such as asthmatic medication, which has an exhalation valve that is closed upon rest or upon inhalation, but which discernably moves to an open position upon exhalation by the patient.

It is a further object of the present invention to provide an exhalation valve in a medication mask which is closed at rest or on inhalation, and which is readily observable as being closed, and which positively opens in a readily discernable manner upon exhalation, which valve is simple and positive, and readily produced at low cost.

In carrying out the principles of the present invention a pediatric mask is provided such as in U.S. Pat. Nos. 4,809, 692 and 4,832,015 mentioned above. The preferred material for molding such mask is silicone rubber. This material can be autoclaved for sterilization, and is well accepted by the medical profession and governmental bodies that might have to approve of the mask. The mask is translucent, and hence it is possible to see at least a limited distance therethrough. In a preferred form of the invention a valve member, is also molded of silicone rubber and is assembled with the balance of the mask by means of an insert and pull operation, with no added fastener being required. In a second form of the invention the valve is molded as an integral part of the mask. Other types of observable one-way air valves are contemplated but the two herein are sufficient for illustration.

THE DRAWINGS

The invention will best be understood with reference to the following specification when taken in connection with the accompanying drawings wherein:

FIG. 1 is a side view of a preferred form of mask having an exhalation valve therein;

FIG. 2 is a view taken from the right side of FIG. 1, comprising an end view of the mask;

FIG. 3 is a view similar to FIG. 2 but before installation of the valve;

FIG. 4 is a sectional view of the valve and a portion of the mask on an enlarged scale as taken along the line 4—4 in FIG. 3;

FIG. 5 is an end view of the valve and adjacent portion of the mask as taken from the right end of FIG. 4 on a further enlarged scale;

FIG. 6 is a perspective view of the mask;

FIG. 7 is a side view on an enlarged scale of the closure member of the valve;

FIG. 8 is a view of the valve closure member as taken from the right side of FIG. 7;

FIG. 9 is an axial sectional view of a second embodiment of the mask;

FIG. 10 is a perspective view of the mask of FIG. 9 as taken from above and the front end:

FIG. 11 is a fragmentary right end view of the valve portion of the mask of FIG. 9 as taken substantially along the line 11—11 in FIG. 9; and FIG. 12 is a top view of the mask of FIG. 9.

DETAILED DESCRIPTION OF THE ILLUSTRATED EMBODIMENTS

Turning now to the drawings in greater particularity, and first to FIGS. 1–8, there will be seen a cylindrical aerosolization chamber 20 (FIG. 1). This chamber is only shown in part, since it may be the same as that shown in Nowacki et al 4,470,412 or in Foley et al 5,012,803, except that the exhalation ports in the aerosolization chamber are deleted. The aerosolization chamber is molded of a semi-rigid plastic, and the exit end thereof is inserted within a gripping ring 22 at the upstream end of a mask 24 molded of suitable material which is sufficiently pliable to conform to an infant's face. A preferred material is translucent silicone rubber. The mask includes a first frustoconical portion 26 of rather shallow taper integral with the ring 22, and a second or downstream portion 28 of frustoconical shape of greater taper. The outer edge 30 (the left edge in FIG. 1) is open, and air and medication flow through the chamber 20 and into the mask as indicated by the arrows 33. The inner surface of the ring 22 is cylindrical and is of small enough diameter to grip the rear end of the aerosolization chamber 20. The mask is circular in outline or cross section, with the exception of a nosepiece 32 and a valve 34, both of which are formed integral with the mask save for an operating or closure member in the valve to be noted hereinafter. The nosepiece 32 extends substantially from end to end of the rearward or portion of greater taper 28, with the frustoconical portion 28 opening radially into the nosepiece. The nosepiece has an outer edge 36 substantially parallel to the corresponding outer surface of the frustoconical portion 28 adjacent to the nosepiece. The nosepiece is substantially an inverted V having legs 38 joined together by an arcuate portion 40 which includes the outer edge 36. At the forward or upstream end the lowest portion of nosepiece 32 is terminated by a vertical wall 42. (The use of "upstream" is intended to refer relative to the air and medication movement through the aerosolization chamber 20 and into the mask 24, as indicated by the arrows 33.)

Forwardly or upstream of the wall 42 there is a boxlike housing 44 extending outwardly from the mask body and closed off therefrom by a portion of the first frustoconical portion 26 and forming a floor 46 to the valve body or housing. Walls 48 extend substantially vertically outwardly from the frustoconical portion 26, and taper inwardly at 50 to a flat roof 52. The upstream end of the valve body 44 is open at 54, and the downstream end of the housing is integrally sealed to the wall 42.

The wall 42 is provided with a small central opening 56 and with a pair of arcuate openings 58 concentric with and spaced horizontally from the smaller central opening 56.

A valve closure member 60 is seen best in FIGS. 7 and 8, and includes a circular head 62. The head is molded so as to be convex on the outer surface 64, and concave on the undersurface 66. Inwardly or rearwardly from the convex inner surface 66 a stem 68 extends rearwardly along the axis of the head 62. The stem somewhat closer to the undersurface 66 than to the outer end 70 of the stem is provided with an integral annular ring or enlargement 72 having a semicircular cross section.

The diameter of the stem 68 is exactly the same as the diameter of the central hole 56, and the distance from the undersurface 66 of the head 62 to the confronting edge of the enlargement 72 is the same as, or very slightly less than the thickness of the wall 42. Accordingly, to assemble the valve head 60 with the mask the end of the stem 70 is pushed through the hole 56 from the upstream surface of the wall 42. Since the enlargement 72 is spaced closer to the undersurface 66 of the valve head than it is to the outer end 70 of the stem, the outer end 70 projects through the wall 42 by the time the enlargement 72 engages the front surface of the wall. The stem adjacent the outer end 70 thus can be grasped and pulled through the hole 56. Stretching of the stem 68 somewhat reduces its diameter. The enlargement 72 is squashed inwardly by the hole 56, while the hole 56 is somewhat enlarged on a temporary basis by the enlargement 72. Thus, the enlargment 72 moves through the wall to abut the rear surface thereof as shown in FIG. 4 to hold the valve member 60 in place. The undersurface 66 of the valve head 62 is flattened against the flat front surface of the wall 42 as shown in FIG. 4. Accordingly, no air can pass through the valve structure from the upstream end (the right end in FIG. 4, for example) into the mask. However, when the infant exhales the pressure within the mask is increased. This increased pressure cannot cause backflow into the aerosolization chamber 20 due to the provision of a one-way valve near the exit end (downstream end) of the aerosolization chamber. However, the air pressure passes air through the arcuate openings 58, flexing the head 62 away from the arcuate openings 58 as shown in broken lines in FIG. 4, thereby permitting exhalation by the infant. Subsequent rest or inhalation by the infant returns the interior of the mask to ambient air pressure or below, and the valve head 62 again flattens against the wall 42.

Flexure of the valve head 62 over the openings 58 is somewhat as if there were two doors pivoted about one or more vertical axes passing through or adjacent to the smaller hole 56. Such movement readily can be seen by a healthcare provider (or the infant's mother) looking into the valve body through the open end 54, or looking through the translucent walls 48, 52 of the valve body. Thus, observation of exhalation is positively assured, and there cannot be exhalation unless there is first inhalation. Thus, it is readily ascertained that the infant is breathing and inhaling the desired medication. All of the parts are large enough to resist rupture or tearing without difficulty, and are readily molded. Installation of the valve member is quick and simple, and adds very little to the overall cost of the mask. No particular close tolerances must be held to provide an integral part of the mask that must flex as has been done in at least some of the prior art.

A modification of the invention is shown in FIGS. 9–12. Many of the parts are similar to those heretofore shown and described, and are identified by the use of similar numerals with the addition of the suffix a to avoid repetition of disclosure. The mask 24a is in most respects substantially the same as that disclosed and claimed in the aforesaid U.S. Pat. No. 4,832,015, but omits the flexible bubble previously used as an indicator of breathing by an infant.

An exhalation valve 34a is molded integrally with the remainder of the mask. It opens at its rear into the nosepiece 40a, and is of the type known as a duckbill valve. It include a forwardly extending generally cylindrical section 76 tapering inwardly at a thinning frustoconical section 78 to a reduced diameter cylindrical section 80. The duckbill valve 34a then steps inwardly at 82 to a thinned forwardly projecting bill 84 terminating at a flat nose 86 having a slit 88 (FIG. 11) extending horizontally across it. The slit 88 is normally closed as shown by the solid line in FIG. 11. Upon inhalation pressure within the mask is reduced, below ambient pressure, and the thinned side portions 84 adjacent the flat nose 86 tend to come together further to close the valve to prevent ingress of air. However, upon exhalation the slit 88 bows outwardly as shown by the broken lines 90 in FIGS. 9 and 11, whereby air readily exits from the exhalation valve 34a.

Both forms of the invention as herein shown and described positively prevent ingress of air through the exhalation valve, and afford egress thereof at very little pressure above ambient pressure, less than 0.50 inch of water. Since the second form of the invention in FIGS. 9–12 has the entire valve formed as an integral part of the mask no assembly step is required in producing the mask. However, molding is somewhat more difficult. In the first and preferred form of the mask as shown in FIGS. 1–8 the assembly step is extremely simple, and does not require much additional labor. Molding is greatly simplified. As has been noted earlier the enlargement 72 on the valve stem 68 avoids the necessity of any separate fastener to hold the umbrella-like valve in installed position, yet is easily moved to installed position. The valve in the first embodiment also opens readily on exhalation with less than 0.50 inch of water internal pressure above ambient, and provides positive closure against entrance of air upon inhalation. It will be appreciated that it is not desired to have air enter upon inhalation as it would dilute the medication being brought in from the aerosolization chamber 20. Exit of air through the two openings or ports 58 provides for passage of a generous amount of exhaled air.

The mask and valve are intended primarily for use with an infant or young child, and in both instances the opening of the valve is readily seen by a healthcare provider, either professional or a parent.

The mask is intended primarily for use with infants and small or young children. Approximate dimensions for the mask are just over 3 inches diameter across the rear, open end 30 and just over two inches from this rear open end 30 to the front of the ring 22 gripping the aerosolization chamber. The inside diameter of the ring 22*a* is approximately 1.4 inches, while the wall thickness is on the order of 0.08 inch. The diameter of the valve head 62 is 0.440 inch and the thickness is 0.015 inch. The length of the valve stem 68 is 0.280 inch from the underside of the head to the end 70. The radius of the valve stem is 0.040 inch, except at the enlargement 72 where the outside diameter is 0.070. The radius of the enlargement (in axial section of the stem) is 0.015 inch.

As noted earlier, the valve opens with a very slight air pressure. An inhalation pressure of 0.5 inch of water below ambient pressure is sufficient to open the valve. Furthermore, the valve is recessed sufficiently as to avoid damage by searching fingers. Damage to the valve that would inhibit operation is thereby positively avoided. The valve is recessed by at least the diameter of the valve.

The mask fits very closely to the face, an d the nosepiece adds little volume. Thus the total volume of the mask is not very great. Accordingly, the medication in the mask, including the nosepiece, is a minimum. The amount of air exhaled is not very great, and previously inhaled air with medication stays for inhalation by the patient. This is an important feature of the present invention. Air held in the mask by the inhalation valve (provided by the valve in the aerosolization chamber), and by the exhalation valve in the mask is retained for a second inhalation. No medication is wasted. With each breath the medication laden air is refreshed for further inhalation by the patient, and is reinforced with the addition of fresh medication laden air.

With every breath, fresh air laden with medication enters the mask from the aerosolization chamber. This air enters the mask adjacent the mouth and nose. There is very little dead space withing the mask. Thus substantially all of the medication laden air is available for inhalation. The medication laden air is retained within the mask by the inlet and outlet valves is available for further inhalation. The amount expelled from the mask by exhalation is just equal to fresh air with medication drawn into the air by inhalation, so that the medication is held close to the patient's face for subsequent inhalation. Very little is wasted.

As noted earlier there are some adult patients who must inhale medication, but are for one reason or another incapable of handling an aerosolization chamber and MDI personally. A similar mask of slightly larger size would be in order for such patients, with a healthcare provider or friend to observe the opening of the valve upon exhalation, and closure upon inhalation.

Particularly in the preferred form of the invention the exhalation valve is located directly adjacent the nostrils, and thereby forms a short path for exhalation from the mask.

The specific embodiments of the invention as herein shown and described are for illustrative purposes only. Various changes in structure will no doubt occur td those skilled in the art, and will be understood as forming a part of the present invention insofar as they fall within the spirit and scope of the appended claims.

What is claimed is:

1. A mask for the inhalation of medication comprising:

a front portion having an inlet adapted for connection to a source for providing an aerosol medication, wherein said mask has minimal dead space inside yet provides efficient inhalation and exhalation flow paths that purge said mask of exhaled air;

a side wall expanding outwardly from said front portion to a rear portion adapted to fit sealingly on a human face;

a wall located adjacent said front portion, and a valve integrally formed in an opening in said wall, wherein said wall and said valve form a single piece of material, said valve adapted for positioning adjacent nostrils of a nose; and wherein said valve is adapted to permit air flow through said opening upon a patient breathing in a first direction, and to prevent air flow through said opening upon the patient breathing in a second direction opposite the first direction and wherein said valve comprises an exhalation valve in fluid communication with an extension projecting from said side wall.

2. The invention of claim 1, wherein said exhalation valve comprises a duckbill valve.

3. The invention of claim 1, wherein said mask comprises a translucent material.

4. A mask for use with an aerosol delivery device, the mask comprising:

an inlet for receiving an end of a medication aerosol delivery device, said inlet adapted for substantial alignment with a mouth of a patient wearing said mask;

a nosepiece integral with said mask, said nosepiece projecting outwardly from a wall of said mask, and adapted to extend over a nose of a patient wearing said mask;

an exhalation valve located adjacent said nosepiece, said exhalation valve adapted for positioning adjacent the nostrils of the nose, said exhalation valve comprising a one-way valve to permit air flow out of said mask upon exhalation, and to prevent air from entering into said mask upon patient inhalation; and wherein said mask is adapted to cover the mouth and nose of the patient and further wherein said exhalation valve is integral with said wall of said mask, said wall and said exhalation valve comprising a single piece of material.

5. The invention of claim 4 wherein said exhalation valve comprises a duckbill valve.

6. The invention of claim 4 wherein said nose piece comprises an extension and said exhalation valve is recessed in said extension.

7. The invention of claim 6 wherein movement of said exhalation valve in response to exhaled air is visible through a wall of said extension.

8. The invention of claim 6 wherein said exhalation valve is recessed in said extension a distance of at least a diameter of said exhalation valve.

9. The invention of claim 6 wherein the extension extends substantially to an end of said mask adjacent to said inlet.

10. The invention of claim 6, wherein said mask further comprises a first frustoconical section and a second frustoconical section, a first end of the first frustoconical section adapted for contact with a face and said second frustoconical section connected with the first frustoconical section, wherein said tunnel-like extension extends longitudinally along said first frustoconical portion and said second frustoconical portion.

11. A mask for use with an aerosol delivery device, the mask comprising:
    an aerosol inlet configured for positioning substantially in front of a mouth of a patient wearing said mask, said aerosol inlet adapted for receiving a source of aerosol medication;
    said mask adapted for fitting over said mouth and a nose of said patient, said mask comprised of a first frustoconical portion of first taper and a second frustoconical portion of a greater taper than said first frustoconical portion; and
    a one-way valve recessed in an extension projecting outwardly from said mask and surrounding an opening in said mask adjacent nostrils of said patient, said one-way valve operative to prevent air flow through said opening in a first direction, but which permits air flow through said opening in a second direction, wherein said extension prevents tampering with said one-way valve.

12. The invention of claim 11 wherein said extension extends longitudinally along said first frustoconical portion and said second frustoconical portion.

13. The invention of claim 11 wherein said one-way valve is recessed in said extension a distance of at least a diameter of said one-way valve.

14. The invention of claim 11 wherein said extension extends substantially to said aerosol inlet of said mask.

15. The invention of claim 11 wherein said one-way valve comprises a circular head.

16. The invention of claim 11 wherein said one-way valve is convex on an outer surface and concave on an inner surface.

17. The invention of claim 11 wherein said one-way valve includes a valve head having an undersurface which is flattened against a flat front of a wall in said mask.

18. The invention of claim 11 wherein said second valve has a slit that bows out.

19. The invention of claim 11 wherein said mask is just over three inches in diameter across a rear thereof.

20. The invention of claim 11 wherein said mask is just over 2 inches from a rear open end to said aerosol inlet.

* * * * *